United States Patent [19]

Gleissle

[11] Patent Number: 5,172,585
[45] Date of Patent: Dec. 22, 1992

[54] CONTINUOUSLY OPERATING CAPILLARY RHEOMETER APPARATUS WITH MINIMIZED RESPONSE-TIME LAG

[75] Inventor: Wolfgang Gleissle, Hagenbach, Fed. Rep. of Germany

[73] Assignee: Göttfert-Werkstoff-Prüfmaschinen GmbH, Buchen, Fed. Rep. of Germany

[21] Appl. No.: 547,762

[22] Filed: Jul. 3, 1990

[30] Foreign Application Priority Data

Jul. 3, 1989 [DE] Fed. Rep. of Germany ....... 3921841

[51] Int. Cl.$^5$ ............................................. G01N 11/04
[52] U.S. Cl. ....................................................... 73/54.04
[58] Field of Search ....................................... 73/55, 56

[56] References Cited

U.S. PATENT DOCUMENTS

| | | | |
|---|---|---|---|
| 2,700,891 | 2/1955 | Shafer | 73/55 |
| 3,116,630 | 1/1964 | Piros | 73/55 |
| 3,559,464 | 2/1971 | Foust et al. | 73/55 |
| 4,442,704 | 4/1984 | Swearingen | 73/55 |
| 4,817,416 | 4/1989 | Blanch et al. | 73/55 |
| 4,932,242 | 6/1990 | Kawashima et al. | 73/55 |

FOREIGN PATENT DOCUMENTS 1801407 11/1971 Fed. Rep. of Germany .
8709717 12/1988 Fed. Rep. of Germany .
3841312 6/1990 Fed. Rep. of Germany .

Primary Examiner—Hezron E. Williams
Assistant Examiner—Joseph W. Roskos
Attorney, Agent, or Firm—Kenyon & Kenyon

[57] ABSTRACT

A capillary rheometer for measuring the viscosity of a liquid contained in a vessel in either a continuous or discontinuous fashion provides timely and accurate measures of viscosity. Pressure sensing means are disposed at one or both ends of a capillary. The capillary is fed fluid by a metering pump, which in turn is fed fluid by a supply pump, the inlet of which is configured for attachment with a fluid sampling port of the vessel and the outlet of which is configured to return sample fluid which was not directed through the capillary back to the liquid or the vessel respectively. The output end of the capillary may be connected to a pump for withdrawing fluid from the capillary. The supply pump and the metering pump may be adjusted independently of each other.

9 Claims, 1 Drawing Sheet

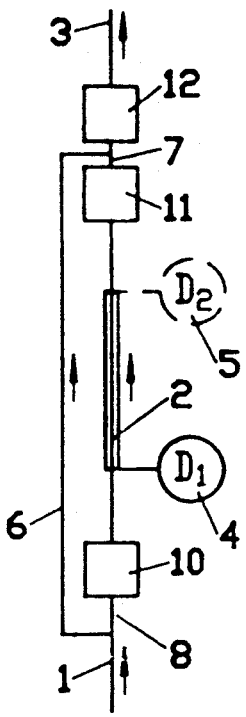
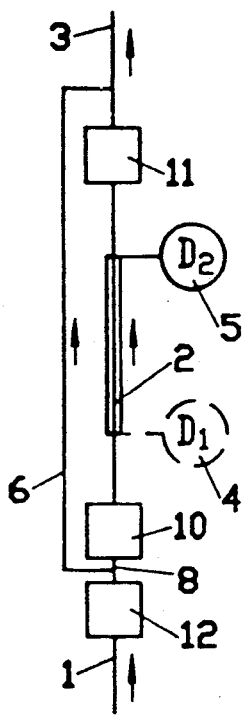
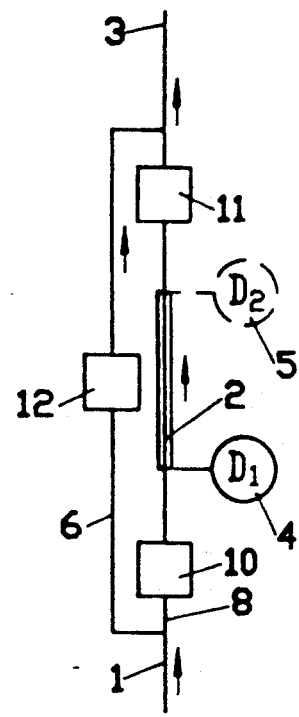
Fig. 1  Fig. 2  Fig. 3
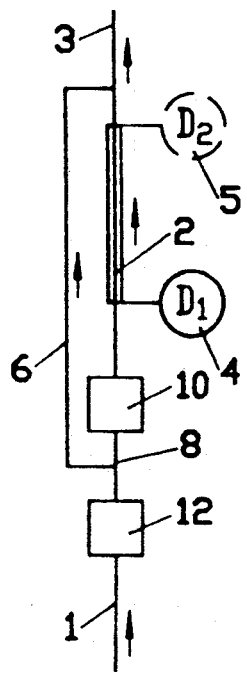
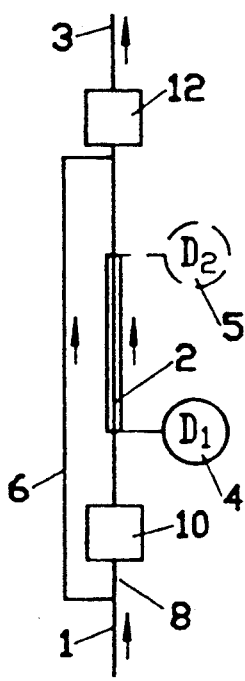
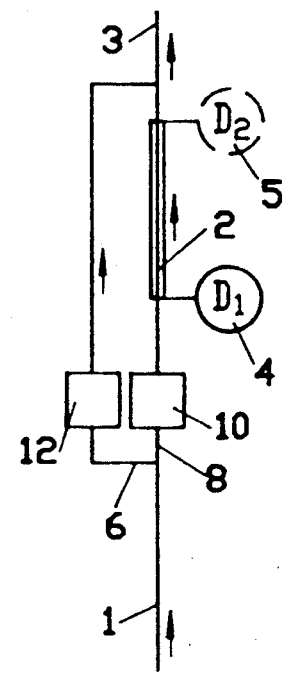
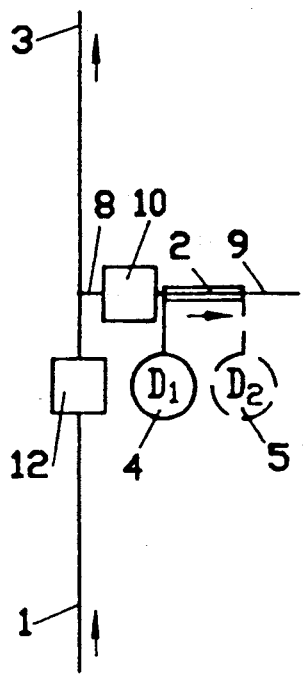
Fig. 4  Fig. 5  Fig. 6  Fig. 7

CONTINUOUSLY OPERATING CAPILLARY RHEOMETER APPARATUS WITH MINIMIZED RESPONSE-TIME LAG

BACKGROUND OF THE INVENTION

The invention relates to fluid measuring devices, and more particularly to continuously operating fluid viscosity measuring devices, such as rheometers.

It is frequently desirable to measure the viscosity of fluids during the course of a chemical process or at other times. The viscosity information obtained from such a measurement may be of immediate or future use. Such data can provide an indication of the quality of a fluid, which can yield information indicative of the extent of a chemical process step, as viscosity is often indicative of a fluid's chemical state. Such information may be used to control the continued operation of the process, especially if the information can be obtained in a timely enough fashion so as to be useful in determining whether the process should continue unaltered or if it should be halted. Alternatively, information related to the quality might be an important aid in determining the future disposition of the liquid, whether such disposition be related to the categorization, grading or determination of the suitability of the liquid for further use.

Information relating to the extent of a process step (such as the extent of chemical conversion or mixing) would be useful in judging the efficacy of a processing step.

In general terms, when liquids which exhibit ideal, or "newtonian" behavior, the viscosity is proportional to the pressure differential across a fluid flow. Thus, by knowing the system variables, the viscosity may be easily derived. However, it is much more common for liquids to exhibit non-newtonian behavior, especially when the liquids are characterized as visco-elastic, such as polymer melts. In the case of non-newtonian liquids, the use of a capillary rheometer apparatus is possible, but calibration measurements for the regime of non-newtonian behavior must be made before the capillary rheometer apparatus can be used to determine viscosity.

In using a capillary rheometer apparatus to determine the viscosity of a liquid exhibiting non-newtonian behavior, data concerning the volumetric flow rate and the pressure differential must be collected. This is because the viscosity is a function of the shear velocity, which by application is a function of the volumetric flow rate, "V", through the capillary. In order to be effective, for non-newtonian liquids, the pressure differential or drop, resp., must be varied over the largest possible range in order to precisely determine the viscosity function. This requires that the volumetric flow rate be varied over a broad range, preferably over several orders of magnitude so as to provide useful data. This is especially desirable because differences in the viscosity of two chemically similar materials is higher for small shear rates than at higher shear rates. This relationship is especially true in the case of high polymer melts.

If the pump in the rheometer apparatus should operate by a constant rotational rate or a constant pressure to determine the viscosity, then it should operate under the conditions of lower shear forces. To achieve this, the liquid to be characterized is first transferred from the reactor by a connection means, typically a tube or pipe, to the rheometer apparatus which comprises a pump and a capillary. From the rotational rate of the pump, the volumetric flow rate of the liquid may be established, and from the measured pressure drop across the capillary, data may be collected from which the viscosity may be determined. Two data collecting methods are available.

The first method requires that the pump be maintained at a constant rotational speed, which provides a constant volumetric flow rate through the capillary, and that pressure drop data over the capillary be collected. For generating this data, the pump's rotational speed is varied between discrete rotational rates over ranges which should encompass three or four orders of magnitude. For example, one such range might be between 0.1 RPM and 100 RPM, a variation on the order of 1000, or three orders of magnitude, where the slowest rotational rate is onethousand times smaller than the fastest rotational rate. This first method is the one most commonly used for rheometric measurements.

The second method of collecting the data requires the generation of a constant pressure drop over the capillary, and is the most frequently used method for the determination of the viscosity of plastic melts. A constant pressure upon the liquid may be achieved, for example, through the use of a constant mass loaded upon a test cylinder. In accordance with the aforementioned calibration of the capillary, a constant internal shear stress is generated in the fluid. The dependent value in the measurement process here is the volumetric flow rate. The appropriate measuring instrument here is the so-called "melt indexer" and its measuring procedure is a process which is standardized worldwide. The value determined from the measurement process, the "melt flow index" (MFI) is determined for a sample of the discharged liquid for a ten minute interval. The units of measurement of the melt flow index are g/10 minutes, or $cm^3$/10 minutes. For the analogous measurement with the use of a metering pump, it is required that the rotational speed of the pump be specifically controlled to establish a constant pressure differential, where the rotational rate is varied across four orders of magnitude.

In the field of capillary rheometers for the continuous measurement of viscosity of liquids in reactors, mixers, extruders or other such process vessels or devices, it is necessary to use a metering pump for withdrawing the liquid from the reactor or the like and pressuring it through the capillary. By this means, the pressure differential over the length of the capillary will be determined. The liquid will may thereafter be allowed to exit (as in a bypass rheometer), or it may be returned to the reactor (as in a parallel flow rheometer). In either form, the rheometer represents a closed system whose overall through-put will be established by the metering pump.

The viscosity of many fluids depends not only on the shear rate but also on the hydrostatic pressure. In case of parallel flow rheometers servicing variably pressured reactors, the viscosity measurement must be decoupled from the pressure within the reactor. To eliminate this pressure dependency, one may provide a second overstepping pump downstream of the capillary and activate it, wherein the output duty of the second pump is greater than that of the metering pump, and which reduces the output pressure of the capillary to or near zero. One such system of this type is known from U.S. Pat. No. 3,548,638 to Uchida, et al. for an "Apparatus and Method for Continuously Determining Viscosity".

Nevertheless, with both of these arrangements, those with or without the second pump, the rotational rate of the pumps must be variable over a range of several orders of magnitude as the flow rate through the rheometer's capillary and connecting means is equally large and proportional to the rotational rate of the metering pump. With the change of the rotational speed, the volumetric flow rate varies in proportion to the rotational rate of the metering pump, which must be changeable over many orders of magnitude. With the change in rotational speed, for example, the average residence time varies inversely with the volumetric flow rate. For example, if the rotational speed is reduced by a factor of 500, then the residence time increases 500 fold. A speed reduction by a factor of 100 would lead to an increase in residence time by a factor of 100. The specific volumetric flow rate of rotary pumps lie about between 0.5 cm$^3$/rpm and 3.2 cm$^3$/rpm. Typical maximum long term rotational speeds of rotary pumps are approximately 100 rpm.

One known embodiment uses about 40 cm$^3$ of fluid in a sidestream capillary rheometer between the test port and the end of the capillary. The metering pump supplies 0.65 cm$^3$/rpm. To cover the range of a normally occurring melt index range (DIN 53 735; $0.1 = <MFI = <50$) at a constant pressure differential, the rotational speed must be variable at least between 100 rpm and 0.2 rpm. This would lead to a range of the intermediate residence time from approximately 37 seconds to over 5 hours, which not only shows, that this range cannot be controlled, but rather also that, the control of the variation of the melt in a narrower range during the process or reaction for continuous process control is not possible, or is, at best, highly imprecise. Further, the measurement should not occur long after the sampling, as the polymer melt is usually not sufficiently stable to bear a high process temperature for a very long time without a change in its molecular structure (thermal degradation).

Minimally, to obtain somewhat useable results where there are no large variations in the viscosity, one chooses the smallest possible transport volume through the capillary by, for example, direct attachment of the capillary rheometer to the chemical process vessel. But this direct attachment is not without attendant difficulties, and is of limited use because there are problems associated with the handling and/or heating or cooling of a rheometer so attached. It has also shown itself, that the suction volume before the metering pump is always at least ten times larger than the volume of the capillary and the volume of the metering pumps (2 to 5 cm$^3$). The transport time through this necessary section of the rheometer apparatus is therefore ten times longer than the actual measuring time during which the fluid flows through the capillary. Therefore, a small residence time may be achieved only through the optimized construction of the rheometer and its immediate connection to the chemical process vessel, via the testing port. Nonetheless, under these circumstances, the establishment of a smaller ratio is generally not possible. This means that the response time of the rheometer is determined mainly by the connecting pipe and not by the rheometer.

With a newtonian liquid, the shear velocity of equivalent volume streams is inversely proportional to the third power of the capillary's inner diameter or measure of internal annular cross section. After the minimization of the volume of the connecting pipe, the expansion of the capillary's inner diameter or measure of internal annular cross section is a further known method to minimize the necessary residence time of the liquid passing through the rheometer apparatus, as this assures minimal residence time by small shear vector. However, this means that liquids with relatively large melt indices can no longer be measured because first, the rotational speed of the metering pump would be exceeded, and second, energy transmitted through the pump to the liquid would cause a transition to impermissibly high temperatures. In order to measure liquids having relatively large melt indices, the capillary used must be provided with a varying diameter. The substitution of a first capillary with a second capillary having a different diameter is not possible during the control of a process, because the time required to effect this change with presently known capillary rheometer arrangements requires that the capillary be once again recalibrated by use of a liquid with known viscosity for use with non-newtonian liquids.

Thus, from the foregoing discussion it is clear that here remain many problems in the art dealing with the viscosity determination of liquids, especially for fluids which exhibit non-newtonian behavior, including those fluids known to the art as polymer melts. The art therefore requires an improved apparatus for use in the determination of liquid viscosity, particularly for polymer melts whose operating characteristics exhibit an advance over devices known to the prior art.

SUMMARY OF THE INVENTION

The present invention provides a novel capillary rheometer apparatus suitable for continuous operation. It also provides a capillary rheometer apparatus which comprises a bypass line arrangement which is parallel to that of the capillary. The device includes a capillary rheometer apparatus that provides for a rapid determination of the viscosity of a test fluid. This is achieved by reducing the residence time of the fluid within the rheometer apparatus, thus minimizing the response time at each stage of operation. The present invention also uses a rheometer apparatus arrangement whose mode of utilization reduces the likelihood of thermal degradation of the liquid sample by reducing the residence time.

Further features, advantages, and embodiments of the invention are apparent from consideration of the following detailed description, drawings, and appended claims.

BRIEF DESCRIPTION OF THE DRAWINGS

FIG. 1 shows a first embodiment of the present invention having a side-stream arrangement.

FIG. 2 shows an alternate construction of the first embodiment of the present invention with a side-stream arrangement.

FIG. 3 shows a second alternate embodiment of the present invention having a side-stream arrangement.

FIG. 4 shows another embodiment of the present invention having a side-stream arrangement.

FIG. 5 illustrates an alternative construction of the rheometer apparatus according to the present invention.

FIG. 6 shows another embodiment of the present invention with a side-stream arrangement.

FIG. 7 illustrates an embodiment of the present invention including a bypass arrangement.

DETAILED DESCRIPTION

The invention will now be described with specific reference to the drawings wherein reference numbers designating like parts will be used throughout the embodiments illustrated in FIGS. 1-7 for the purposes of consistency and clarity. References to "upstream" and "downstream" are to indicate positions relative to one another with regard to the direction of flow of the fluid streams, with the arrows in each of the Figures indicating the direction of fluid flow from "upstream" to "downstream" positions.

Turning now to FIG. there is shown a first embodiment of the present invention having a side-stream arrangement. The liquid to be tested is withdrawn from the test port or other port, connection, or orifice suitable for withdrawing liquid from the process vessel (not shown). The chemical process vessel may be any reactor, mixer, extruder or other device in which the liquid to be tested is contained, and will usually be simply referred to as the reactor. The liquid to be tested and withdrawn from the reactor will be transmitted via a feed line (1) and a metering pump (10) to a capillary (2), and thereafter will pass to a withdrawal pump (11) which is connected by a connection line (7) to a supply pump (12) and may be withdrawn through an output line (3). (The supply pump and the metering pump in this and other embodiments may be adjusted independently of each other.) For the determination of the pressure differential along the length of the capillary (2), there is further provided a first pressure measuring line (4) at the entrance to the capillary (2), and a second pressure measuring line (5) at the exit of the capillary (2). It should be apparent to those skilled in the art that both the first pressure measuring line (4) and the second pressure measuring line (5) may be any pressure measuring device normally used with rheometers, or may be any connection line, tube, conduit, transducer or the like which may be located at one or both of the ends of the capillary (2). Additionally, there is provided a by-pass line (6) whose first end is connected to the feed line (1) before the inlet to the metering pump (10) and whose second end is connected to the connection line (7) interposed between the output of the withdrawal pump (11) and the input of the supply pump (12). For the elimination of the effects of pressure within the chemical process vessel on the measurement of the viscosity in the capillary (2), two pumps are contemplated. Along with the metering pump (10), the withdrawal pump (11) has the function of isolating the capillary (2) from the pressure within the reactor. The withdrawal pump (11) is to preferably have a throughput capacity which slightly exceeds that of the metering pump (10). Further, the connection line (8) between the withdrawal point of the measurement stream to the rheometer from the feed line (1) and the bypass line (6) is as short as possible.

FIG. 2 illustrates an alternative embodiment of the invention, which includes an arrangement wherein the supply pump (12) is connected to the metering pump (10) at a point upstream from the metering pump (10), and the bypass line (6) is connected to the connection line (8) between these two pumps.

The capillary (2) may be one of the type which has dimensions usually encountered in capillary-rheometers. With capillaries whose inner annulus have circular cross-sections, commonly encountered inner diameters lie within the range of about between 0.1 and 8 millimeters (mm), and overall lengths lie in the range of about 5.0 mm and 100.0 mm. Capillaries having non-circular inner annuli may also be utilized, such as those having rectangular cross sections wherein the inner annulus has a width within the range of about 5.0 mm and 20.0 mm, and those having a depth within the range of about 0.20 mm and 4.0 mm. Both of these types of capillaries may be used in the practice of the invention, and may be interchanged.

When a withdrawal pump (11) has a throughput greater than that of the metering pump (10) employed, a measurement of the pressure at the output of the capillary is not necessary, as the pressure at the inlet of withdrawal pump (11) is negligibly small. Through the utilization of the bypass (6), the volumetric stream in the feed line (1) and in the output line (3) are of a constant quantity and is independent from the throughput of the metering pump (10). The rotational direction of the pump may be freely selected, which means that the supply pump (12) may be positioned downstream from the withdrawal pump (11) (as is illustrated in FIG. 1), or it may be positioned upstream from the metering pump (10) (as shown in FIG. 2). In both alternate arrangements the direction of the rotation of the impeller (or other fluid pumping means within the pump) should be selected and established so as to assure that the direction of the throughput of the supply pump (12) is in the direction of the fluid flow.

Another advantageous embodiment is illustrated in FIG. 3, wherein the supply pump (12) is positioned within the bypass line (6). With such an arrangement, when the metering pump (10) and the withdrawal pump (11) have respectively small rotational speeds, one retains by the constant rotational speed of the supply pump (12) a minimal throughput stream. When the measurement of the viscosity is performed by maximum shear rates, the total liquid flow is at the highest rate that will be achieved in an extremely short operating time. With this arrangement, a constant throughput stream can be achieved through the appropriate proportional limitation of the rotational speed of the supply pump (12) relative to the rotational speed of the metering pump (10) and the withdrawal pump (11). One may also substitute a plurality of capillaries for the capillary (2) according to FIG. 3.

With particular throughput rates, the viscosity measurement can be attained independently of the necessity of measuring the process pressure, as when the liquid has a viscosity which is independent of the effect of pressure, or where one would like to determine the viscosity at an instantaneous process pressure. In such cases, one may dispose of the withdrawal pump (11). The capillary (2) is then open at the one end opposite to that of the reactor. It is then as a rule advantageous to measure the pressure differential utilizing two pressure measuring lines (4, 5). FIGS. 4 through 6 show such advantageous configurations of the metering pump (10) and the supply pump (12) relative to the capillary (2).

FIG. 4 illustrates an embodiment wherein the supply pump (12) is upstream from both the metering pump (10) and the upstream inlet of the bypass line (6). This fourth embodiment provides a constant overall throughput stream as in FIG. 1 and a constant residence time for the complete system.

FIG. 5 illustrates an embodiment wherein the supply pump (12) sucks in the liquid from both the capillary (2) and the downstream outlet of the bypass line (6) to which it is connected.

FIG. 6 illustrates the parallel connection of the metering pump (10) and the supply pump (12) of the bypass line (6). This embodiment yields the shortest possible residence time for continuous viscosity measurement of all the embodiments discussed above and represented in FIGS. 1-5. A constant throughput stream rate may be achieved by setting and regulating the rotational speed of the supply pump (12).

FIG. 7 illustrates a still further arrangement that includes a supply pump (12) wherein the sampling time of the capillary is minimized. This embodiment uses an alternative bypass arrangement. In many situations, it is either impossible or not necessary to return the tested liquid back to the reactor. The liquid is then withdrawn beyond the capillary through an output line (9), and then "lost" to the system. Such rheometers are known as "bypass-rheometers". In such an arrangement, the supply pump (12) serves only to rapidly supply the liquid to the metering pump (10). What liquid is not necessary for the viscosity measurement may be returned to the reactor. Thus a continuously measuring bypass rheometer can also operate using small volume streams, i.e., by rapidly determining the viscosity of liquids with high resolution and rapid measurement times.

Although the invention has been described with reference to the several embodiments herein disclosed, it should be apparent that many modifications and variations are possible and are considered to be within the scope and spirit of the inventive concept of the instant invention.

What is claimed is:

1. A capillary rheometer apparatus for the measurement of the viscosity of fluid substances, especially polymer melts and other visco-elastic fluids, comprising:
   a capillary having first and second sides;
   a metering pump for pumping fluid to the capillary in a controlled manner;
   a first connection line for carrying fluid from the metering pump to the capillary;
   a second connection line attached to the input side of the metering pump configured for attaching the metering pump to a fluid sampling port of a vessel containing fluid whose viscosity is to be ascertained;
   a withdrawal pump for pumping fluid from the capillary in a controllable manner;
   means associated with at least one side of the capillary for sensing pressure;
   a bypass line for routing fluid from a point immediately upstream of the metering pump to a point downstream from the output side of the withdrawal pump, whereby the bypass line joins with the output of the withdrawal pump;
   an independently controllable supply pump for assisting in the movement of fluid from the fluid sampling port through the capillary rheometer apparatus, said supply pump and said metering pump being controlled independently of one another; and
   whereby the fluid passing through the bypass line is returned to the vessel from which it was drawn.

2. The capillary rheometer of claim 1, wherein the supply pump inlet is located in an upstream position at which it receives fluid from the fluid sampling port of the vessel, and the outlet of the supply pump is divided among two flows, one directed to the inlet side of the metering pump, and the other to the inlet end of the bypass line.

3. The capillary rheometer of claim 1, wherein the supply pump is located along the bypass line.

4. The apparatus according to claim 1 wherein the means for sensing pressure are associated with only the inlet side of the capillary.

5. A capillary rheometer apparatus for the measurement of the viscosity of fluid substances, especially polymer melts and other visco-elastic fluids, comprising:
   a capillary having first and second sides;
   a metering pump for pumping fluid to the capillary in a controlled manner;
   a first connection line for carrying fluid from the metering pump to the capillary;
   a second connection lien attached to the input side of the metering pump configured for attaching the metering pump to a fluid sampling port of a vessel containing fluid whose viscosity is to be ascertained;
   an independently controllable supply pump for assisting in the movement of fluid through the capillary rheometer apparatus in a controllable manner, said supply pump and said metering pump being controllable independently of one another;
   means associated with at least one side of the capillary for sensing pressure;
   a bypass lien for routing fluid from a point immediately upstream of the metering pump to a point downstream from the output side of the capillary, whereby the bypass line joins with the output of the capillary; and
   whereby the fluid passing through the bypass line is returned to the vessel from which it was drawn.

6. The capillary rheometer of claim 5, wherein the supply pump inlet is located in an upstream position at which it receives fluid from the fluid sampling port of the vessel, and the outlet of the supply pump is divided among two flows, one directed to the inlet side of the metering pump, and the other to the inlet end of the bypass line.

7. The capillary rheometer of claim 5, wherein the supply pump is located along the bypass line.

8. A capillary rheometer apparatus for the measurement of the viscosity of fluid substances, especially polymer melts and other visco-elastic fluids, comprising:
   a capillary having first and second sides;
   a metering pump for pumping fluid to the capillary in a controlled manner;
   a first connection line for carrying fluid from the metering pump to the capillary;
   a second connection line attached to the input side of the metering pump configured for attaching the metering pump to a fluid sampling port of a vessel containing fluid whose viscosity is to be ascertained;
   a withdrawal pump for pumping fluid from the capillary in a controllable manner;
   means associated with at least one side of the capillary for sensing pressure;
   a bypass line for routing fluid from a point before the metering pump to a point downstream from the output side of the withdrawal pump, whereby the bypass line joins with the output of the withdrawal pump;

an independently controllable supply pump for assisting in the movement of fluid from the fluid sampling port through the capillary rheometer apparatus, wherein the supply pump inlet is located downstream from the outlet of the withdrawal pump beyond the point where the bypass line joins with the output of the withdrawal pump, said supply pump and said metering pump being controlled independently of one another; and whereby the fluid passing through the bypass line is returned to the vessel from which it was drawn.

9. A capillary rheometer apparatus for the measurement of the viscosity of fluid substances, especially polymer melts and other visco-elastic fluids, comprising:

a capillary having first and second sides;

a metering pump for pumping fluid to the capillary in a controlled manner;

a first connection line for carrying fluid from the metering pump to the capillary;

a second connection line attached to the input side of the metering pump configured for attaching the metering pump to a fluid sampling port of a vessel containing fluid whose viscosity is to be ascertained;

an independently controllable supply pump for assisting in the movement of fluid through the capillary rheometer apparatus in a controllable manner, said supply pump and said metering pump being controllable independently of one another;

means associated with at least one side of the capillary for sensing pressure;

a bypass line for routing fluid from a point upstream of the metering pump to a point downstream from the output side of the capillary, whereby the bypass line joins with the output of the capillary and wherein the supply pump inlet is located downstream from the point at which the bypass line joins the output of the capillary; and whereby the fluid passing through the bypass line is returned to the vessel from which it was drawn.

* * * * *

UNITED STATES PATENT AND TRADEMARK OFFICE
CERTIFICATE OF CORRECTION

PATENT NO. : 5,172,585

DATED : December 22, 1992

INVENTOR(S) : Gleissle

It is certified that error appears in the above-indentified patent and that said Letters Patent is hereby corrected as shown below:

Column 2    line 16, change "onethousand" to --one thousand--.

Column 5    line 13, change "FIG." to --FIG. 1,--.

Signed and Sealed this

Twenty-eighth Day of June, 1994

Attest:

BRUCE LEHMAN

Attesting Officer    Commissioner of Patents and Trademarks